United States Patent [19]

Fields, Jr. et al.

[11] Patent Number: 4,952,723

[45] Date of Patent: Aug. 28, 1990

[54] PROCESS FOR PRODUCING N-PHOSPHONOMETHYLGLYCINE

[75] Inventors: Donald L. Fields, Jr., Manchester; Raymond C. Grabiak, Maryland Heights; Dennis P. Riley, Ballwin, all of Mo.

[73] Assignee: Monsanto Company, St. Louis, Mo.

[21] Appl. No.: 386,738

[22] Filed: Jul. 31, 1989

[51] Int. Cl.$^5$ ............................................. C07F 9/38
[52] U.S. Cl. ................................................... 562/17
[58] Field of Search ......................................... 562/17

[56] References Cited

U.S. PATENT DOCUMENTS

| | | | |
|---|---|---|---|
| 3,950,402 | 4/1976 | Franz | 260/502.5 |
| 3,954,848 | 5/1976 | Franz | 260/502.5 |
| 3,969,398 | 7/1976 | Hershman | 260/502.5 |
| 4,147,719 | 4/1979 | Franz | 562/17 |
| 4,853,159 | 8/1989 | Riley | 562/17 |

FOREIGN PATENT DOCUMENTS 011706 1/1981 Hungary.
2049697 12/1980 United Kingdom .................. 562/17

OTHER PUBLICATIONS

Endo et al., *Tetrahedron Letters* 26, No. 37, pp. 4525-4526 (1985).
Ledwith, *Accounts of Chemical Research*, 5, pp. 133-139 (1972).
Farrington et al., *Chemical Communications*, pp. 259-260 (1969).
Rieger et al., *J. Org. Chem*, 53, No. 7, pp. 1481-1485 (1988).

*Primary Examiner*—J. E. Evans
*Attorney, Agent, or Firm*—Frank D. Shearin

[57] ABSTRACT

A process for the production of N-phosphonomethylglycine comprising contacting N-phosphonomethyliminodiacetic acid with a molecular oxygen-containing gas in the presence of a catalyst selected from the group consisting of the salts and salt complexes of manganese, cobalt, iron, nickel, chromium, ruthenium, aluminum, moleybdenum, vanadium and cerium, and an effective amount of a dipyridyl compound.

25 Claims, No Drawings

PROCESS FOR PRODUCING N-PHOSPHONOMETHYLGLYCINE

BACKGROUND OF THE INVENTION

This invention relates to a process for preparing N-phosphonomethylglycine by the oxidation of N-phosphonomethyliminodiacetic acid using a homogeneous catalyst system. More particularly, this invention relates to a process for producing N-phosphonomethylglycine by the oxidation of N-phosphonomethyliminodiacetic acid using a salt of a selected metal in the presence of a dipyridyl compound.

N-Phosphonomethylglycine, known in the agricultural chemical art as glyphosate, is a highly effective and commercially important phytotoxicant useful in controlling the growth of germinating seeds, emerging seedlings, maturing and established woody and herbaceous vegetation, and aquatic plants. N-Phosphonomethylglycine and its salts are conveniently applied in an aqueous formulation as a postemergent phytotoxicant for the control of numerous plant species. N-Phosphonmethylglycine and its salts are characterized by broad spectrum activity, i.e., the controlled growth of a wide variety of plants.

Numerous methods are known in the art for the oxidation of the N-phosphonomethyliminodiacetic acid to N-phosphonomethylglycine. For example, U.S. Pat. No. 3,969,398 to Hershman discloses a process for the production of N-phosphonomethylglycine by the oxidation of N-phosphonomethyliminodiacetic acid utilizing a molecular oxygen-containing gas as the oxidant in the presence of a catalyst consisting essentially of activated carbon. U.S. Pat. No. 3,950,402 discloses a method where N-phosphonomethyliminodiacetic acid is oxidized to N-phosphonomethylglycine in an aqueous media using a free oxygen-containing gas and a noble metal catalyst, such as palladium, platinum or rhodium on a support. U.S. Pat. No. 3,954,848 discloses the oxidation of N-phosphonomethyliminodiacetic acid with hydrogen peroxide and a acid such as sulfuric acid. Hungarian Patent Application No. 011706 discloses the oxidation of N-phosphonomethyliminodiacetic acid with peroxide in the presence of metals or metal compounds.

The dipyridyl compounds useful in the process of the present invention are known to those skilled in the art to be useful as electron transfer agents. Examples of references for the latter use include: Endo, et al., *Tetrahedron Letters* 26, No. 37, pp 4525–4526 (1985); Ledwith, *Accounts of Chemical Research*, 5, pp 133–139 (1972); Farrington, et al., *Chemical Communications*, pp 259–260 (1969); and Rieger, et al., *J. Org. Chem.*, 53, No. 7, pp 1481–1485 (1988).

Although satisfactory results are obtained by the processes of the prior art to prepare N-phosphonomethylglycine using heterogeneous catalysts such as activated carbon or a noble metal on a support, there is now provided a process for preparing N-phosphonomethylglycine using a homogeneous catalyst system which produces outstanding results through high conversions and selectivities, while minimizing the formation of undesirable byproducts such as phosphate. The process also simplifies separation of the product from the catalyst.

SUMMARY OF THE INVENTION

These and other advantages are achieved by a process for the production of N-phosphonomethylglycine comprising contacting N-phosphonomethyliminodiacetic acid with a molecular oxygen-containing gas in the presence of a catalyst selected from the group consisting of the salts and salt complexes of manganese, cobalt, iron, nickel, chromium, ruthenium, aluminum, molybdenum, vanadium and cerium, and an effective amount of a dipyridyl compound represented by the formula

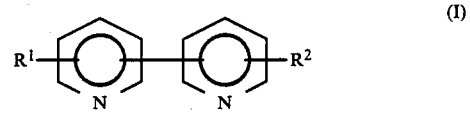

wherein $R^1$ and $R^2$ are independently selected from the group consisting of hydrogen, alkyl having from one to about 18 carbon atoms, ortho-phenylene, oxygen, sulfur, $SO_2$, $SO_3$, $N—R^5$ wherein $R^5$ is alkyl having from one to six carbon atoms, and $R^1$ and $R^2$ together can form a bridge with groups selected from alkylene having from one to about six carbon atoms; wherein the alkylene bridge can contain branching or double bonds; or salts thereof represented by the formula

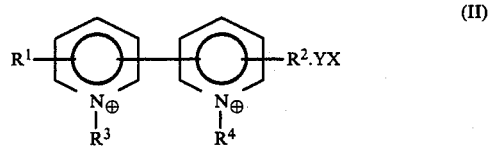

wherein $R^1$ and $R^2$ are as defined above, Y is one or two depending on whether X is a dianion or a monoanion, and X is selected from the group consisting of halide, sulfate and nitrate, phosphate, perchlorate, and the like; and $R^3$ and $R^4$ are individually selected from the group consisting of hydrogen or alkyl having from one to about 18 carbon atoms, and $R^3$ and $R^4$ together can form a bridge with groups selected from alkylene having from one to about six carbon atoms wherein the alkylene bridge can contain branching or double bonds.

DETAILED DESCRIPTION OF THE INVENTION

The process of the present invention involves contacting N-phosphonomethyliminodiacetic acid with a water-soluble salt or a salt complex of selected metals in a mixture or solution in the presence of a dipyridyl compound. The mixture or solution is contacted with a molecular oxygen-containing gas while heating the reaction mass to a temperature sufficiently high to initiate and sustain the oxidation reaction of N-phosphonomethyliminodiacetic acid to produce N-phosphonomethylglycine.

The catalyst in the present invention can be any one or more of the salt and salt complexes of manganese, cobalt, iron, nickel, chromium, ruthenium, aluminum, molybdenum, vanadium or cerium. Suitable salts include manganese acetate, manganese sulfate, manganese(II or III) acetylacetonate, cobalt sulfate, cobalt(II or III) acetylacetonate, cobalt chloride, cobalt bromide, cobalt nitrate, cobalt acetate, ceric ammonium sulfate, ceric ammonium nitrate, ferric ammonium sulfate, and salts such as nickel bromide, chromium chloride, ruthenium chloride, ruthenium bromide, aluminum nitrate, vanadyl sulfate, vanadium bromide, vanadium chloride, and the like. Preferred catalysts are the salt and salt complexes of manganese, cobalt, vanadium and cerium that are soluble under the reaction conditions. Vanadium and cobalt salts are especially preferred.

The catalyst can be added to the N-phosphonomethyliminodiacetic acid in the salt form, or the salt may be generated in situ by the addition of a source of the metal ion, such as manganese dioxide, cobalt oxide or vanadium pentoxide which dissolves in the reaction mixture. Vanadyl sulfate is especially preferred.

The concentration of the catalyst in the process of the present invention can vary within wide limits. The concentration can vary between about 1 molar to about 0.0001 molar total metal ion concentration. For most of the metal salts, the reaction appears to have a first order dependency on the catalyst concentration, i.e. the reaction rate increases linearly as a catalyst concentration increases. The preferred concentration for the catalyst metal ion is in the range of about 0.1 molar to about 0.001 molar which gives a suitably fast rate of reaction that can be easily controlled and favors selectivity to N-phosphonomethylglycine.

The dipyridyl compounds of the present invention are known to the art, and can be represented by the formula

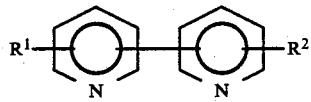

(I)

wherein $R^1$ and $R^2$ are independently selected from the group consisting of hydrogen, alkyl having from one to about 18 carbon atoms, ortho-phenylene, oxygen, sulfur, $SO_x$, $N-R^5$ wherein $R^5$ is alkyl having from one to six carbon atoms, and $R^1$ and $R^2$ together can form a bridge with groups selected from alkylene having from one to about six carbon atoms, wherein the alkylene bridge can contain branching or double bonds.

When $R^1$ and $R^2$ form a bridge, the compounds can be represented by formulas such as

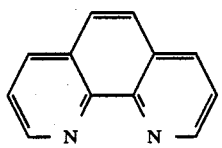

(III)

or

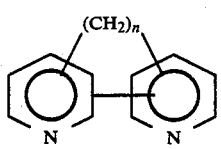

(IV)

where n is from one to about 18.

The salts of the dipyridyl compounds can be used and can be represented by the formula:

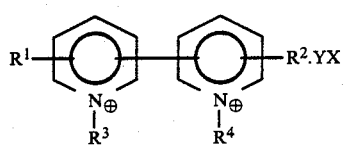

(II)

wherein $R^1$ and $R^2$ are as defined above, Y is one or two depending on whether X is a dianion or a monoanion, and X is selected from the group consisting of halide, sulfate and nitrate, phosphate, perchlorate, and the like; and $R^3$ and $R^4$ are individually selected from the group consisting of hydrogen or alkyl having from one to about 18 carbon atoms, and $R^3$ and $R^4$ together can form a bridge with groups selected from alkylene having from one to about six carbon atoms wherein the alkylene bridge can contain branching or double bonds.

When $R^3$ and $R^4$ form a bridge, the dipyridyl compounds can be represented by the formula:

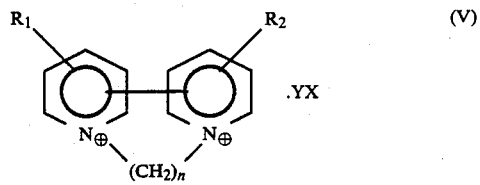

(V)

where n is from one to about 18. It should be noted, however, that the free bases of the 2,2-dipyridyl compounds are not as effective as the other isomers in the process of the present invention due to its rate inhibiting effects.

The compounds represented by Formula II where $R^3$ and $R^4$ are each methyl and X is chloride and y is 2 are preferred, but especially preferred are the compounds of Formula V wherein X is bromide and n and Y are 2.

The concentration of the dipyridyl compound in the process of the present invention can vary within wide limits, depending upon the amount of the catalyst salt and the amount of N-phosphonomethyliminodiacetic acid present in the reaction medium that are used, and the particular dipyridyl compound that is selected. In general, it has been found that the concentration of the dipyridyl compound can vary from about 0.005 molar in the reaction solution to one molar, and higher concentrations of the dipyridyl compound can be used, although such higher concentrations do not seem to have a significant effect on the selectivity of the oxidation of N-phosphonomethyliminodiacetic acid to N-phosphonomethylglycine. It has been found that concentrations of the dipyridyl compound between about 0.01 molar to about 0.5 molar provides satisfactory results, and these are the concentrations that we prefer to use.

The reaction temperature is sufficient to initiate and sustain the oxidation reaction and can vary from about 25° C. to 150° C. In general, as the reaction temperature increases, the reaction rate increases. To achieve an easily controlled reaction rate and favor selectivity of the reaction to the formation of N-phosphonomethylglycine, a preferred temperature range is from about 50° C. to about 90° C. If temperatures above the boiling point are used, pressure should be maintained on the reaction system to maintain a liquid phase.

To carry out the process of the present invention, it is only necessary to bring N-phosphonomethyliminodiacetic acid together with an effective amount of the catalyst salt and an effective amount of the dipyridyl compound in the presence of a molecular oxygen-containing gas. The term "molecular oxygen-containing gas" means molecular oxygen gas or any gaseous mixture containing molecular oxygen with one or more diluents which are nonreactive with the oxygen or with the reactants or the products under the conditions of the reaction. Examples of such diluent gases include air, helium, argon, nitrogen, or other inert gases, or oxygen-hydrocarbon mixtures. A preferred molecular oxygen-containing gas is undiluted oxygen gas.

The oxygen concentration, i.e., the partial pressure of oxygen, affects the reaction rate and selectivity to the desired N-phosphonomethylglycine. As the partial pressure of oxygen increases, the reaction rate generally increases. The partial pressure of oxygen can be increased by increasing the overall reaction pressure or by increasing the molecular oxygen concentration in the oxygen-containing gas. When the partial pressure of oxygen is below about $2.07 \times 10^5$ N/m$^2$ (30 psig) the reaction is somewhat slow, and we prefer to use at least this partial pressure of oxygen. Although there is no upper limit to the partial pressure of oxygen, we have found that satisfactory results can be achieved at a partial pressure of oxygen up to $3.45 \times 10^6$ N/m$^2$ (500 psig), or higher if desired. The preferred partial pressure of oxygen will vary from metal salt to metal salt, and the preferred partial pressure of oxygen for each salt can be determined by routine experimentation.

As will occur to those skilled in the art in view of the present disclosure, the manner in which the solution or mixture of N-phosphonomethyliminodiacetic acid is contacted with a molecular oxygen-containing gas in the presence of the metal salt catalyst and the dipyridyl compound can vary greatly. For example, the N-phosphonomethyliminodiacetic acid solution can be contacted with the oxygen-containing gas by agitation, such as bubbling, stirring, shaking, and the like. The process of the present invention only requires actively contacting the molecular oxygen-containing gas with the aqueous solution or mixture of N-phosphonomethyliminodiacetic acid containing the metal catalyst salt and the dipyridyl compound.

The initial pH of the reaction affects the reaction rate and the selectivity to N-phosphonomethylglycine. The initial pH of the reaction can vary between about pH 0.1 to about pH 7. A preferred range is from about pH 0.1 to pH 3, and a more preferred pH range is the unadjusted pH of the N-phosphonomethyliminodiacetic acid in an aqueous media, which varies with the N-phosphonomethyliminodiacetic acid concentration and the reaction temperature.

The oxidation reaction can take place in a solution or a slurry. For a solution, the initial concentration of the N-phosphonomethyliminodiacetic acid in the reaction mass is a function of the solubility of the N-phosphonomethyliminodiacetic acid in the solvent (i.e. water) at both the desired reaction temperature and the initial pH of the solution. As the solvent temperature and the initial pH changes, the solubility of N-phosphonomethyliminodiacetic acid changes. It has been found that the process of the present invention works with very dilute solutions or even with a slurry of the N-phosphonomethyliminodiacetic acid in an aqueous solution. The reaction is typically carried out in an aqueous solvent, i.e., containing at least about 50 wt. % water. The preferred aqueous solvent is distilled, deionized water.

The invention is further illustrated by, but not limited to, the following examples. In all cases the reactions were conducted in an Autoclave Engineers 300 ml pressure reactor in which a stirrer was installed in the head as were three additional valve ports that were used as a sample port, a gas inlet and purged gas outlet. The stirrer maintained sufficient agitation to afford thorough gas liquid mixing. The indicated amount of catalyst salt and dipyridyl compound was dissolved or suspended in a distilled deionized water solution containing the indicated amounts of N-phosphonomethyliminodiacetic acid. The reactor was sealed, pressurized to the indicated pressures with an oxygen gas sweep at about 300 cc per minute and heated to the indicated reaction temperatures with agitation.

The percent selectivity to N-phosphonomethylglycine was determined by dividing the moles of N-phosphonomethylglycine and N-formyl-N-phosphonomethylglycine produced by the total moles of N-phosphonomethyliminodiacetic acid consumed and multiplying by 100. The percent conversion of N-phosphonomethyliminodiacetic acid was determined by dividing the moles of N-phosphonomethyliminodiacetic acid that were reacted by the total moles of starting N-phosphonomethyliminodiacetic acid and multiplying by 100.

EXAMPLES 1-9

Into the autoclave was added water (100 ml) and N-phosphonomethyliminodiacetic acid (39.2 g, 0.1 mol). Vanadyl sulfate hydrate was added in a sufficient amount to provide the vanadyl sulfate molarity indicated in Table 1. In addition, there was then added a sufficient amount of 1,1'-ethylene-2,2'-dipyridinium dibromide to provide the molarity of the diquat indicated in Table 1. The autoclave was sealed and an oxygen flow through the autoclave was begun at 300 cc/minute. Then, the autoclave was heated to 75° C. with stirring for the indicated times. The results are shown in Table 1.

TABLE 1

| Example | Reactor Pressure (N/m$^2$) | VOSO$_4$ (molarity) | Diquat (molarity) | Time (hours) | Conversion (%) | Selectivity (%) |
|---|---|---|---|---|---|---|
| 1 | $1.38 \times 10^6$ | 0.001 | 0 | 3 | 95 | 59 |
| 2 | $1.38 \times 10^6$ | 0.001 | 0.005 | 2 | 78 | 78 |
| 3 | $1.38 \times 10^6$ | 0.0011 | 0.01 | 2 | 75 | 85 |
| 4 | $1.38 \times 10^6$ | 0.0011 | 0 | 6.5 | 94 | 64 |
| 5 | $1.38 \times 10^6$ | 0.0049 | 0.01 | 3.5 | 82 | 90 |
| 6 | $6.89 \times 10^5$ | 0.0049 | 0 | 6.5 | 84 | 48 |
| 7 | $6.89 \times 10^5$ | 0.0049 | 0.01 | 5.5 | 83 | 94 |
| 8 | $3.45 \times 10^5$ | 0.0049 | 0 | 5.5 | 66 | 41 |
| 9 | $3.45 \times 10^5$ | 0.0049 | 0.01 | 5.5 | 79 | 88 |

EXAMPLE 10

A. To the autoclave was added water (125 ml) and N-phosphonomethyliminodiacetic acid (20 g, 0.088 mol). Cobalt sulfate (1.471 g, 0.0045 mol) was then added to the autoclave which was then sealed and heated to 95° C. and maintained at an oxygen pressure of $1.38 \times 10^6$ N/mz (200 psig) at a constant oxygen flow rate of 300 cc/minute. After 2.5 hours, analysis indicated a conversion of 91% and a selectivity of 58.5%.

B. The procedure of Example 10A was repeated except that 1,1'-dimethyl-4,4'-bipyridinium dichloride (0.351 g, 0.00225 mol) was added to the autoclave along with the cobalt sulfate. After 4 hours, analysis indicated a conversion of 80.3% and a selectivity of 77.6%.

C The procedure of Example 10A was repeated except that 1,1'-ethylene-2,2'-dipyridinium dibromide (0.757 g, 0.0022 mol) was added to the autoclave along with the cobalt sulfate. After 3.5 hours, analysis indicated a conversion of 75.4% and a selectivity of 77.9%.

D. The procedure of Example 10A was repeated except that a compound (0.8057 g, 0.0022 mol) represented by the formula

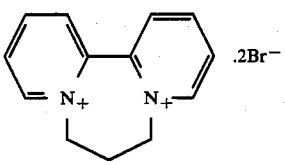

was added to the autoclave along with the cobalt sulfate. After 4 hours, analysis showed that the conversion was 85.1% and the selectivity was 78.6%.

EXAMPLE 11

A. Into the autoclave was added water (100 ml) and N-phosphonomethyliminodiacetic acid (26.7 g). Then cobalt II sulfate 7H₂O (3.3 g) was added. The autoclave was sealed and pressurized to $3.1 \times 10^6$ N/m² (450 psg) and an oxygen flow through the autoclave was begun at 300 cc/minute. The autoclave was heated to 95° C. with stirring for three hours. Analysis showed that there was 99.9% conversion with a selection of 61.5%.

B. The procedure of part A above was repeated except that the 1,1'-dimethyl-4,4'-bipyridinium dichloride (1.5 g) was added to the autoclave. Analysis showed that there was 73.6% conversion with a selectivity of 90.1%.

EXAMPLES 12–18

The procedure of Examples 1–9 was repeated except that different quantities of vanadyl sulfate in water (100 ml) and different dipyridyl compounds were used. The results are shown in Table 2.

TABLE 2

| Example | Dipyridyl Compound Formula | (g) | Reactor Pressure (N/m²) | VOSO₄ (g) | Temp. (°C.) | Time (hours) | Conversion (%) | Selectivity (%) |
|---|---|---|---|---|---|---|---|---|
| 12 | none | none | 3.1 × 10⁶ | 3.8 | 80 | 1 | 97.7 | 51.0 |
| 13 | [structure] | 2.4 | 3.1 × 10⁶ | 1.2 | 70 | 2.5 | 99.2 | 84 |
| 14a | [structure] | 1.5 | 3.4 × 10⁵ | 1.0 | 80 | 1 | 74.3 | 88.4 |
| 15 | [structure] | 2.0 | 3.1 × 10⁶ | 1.0 | 75 | 2 | 94.5 | 69.9 |
| 16 | [structure] | 2.6 | 3.1 × 10⁶ | 1.2 | 70 | 2 | 93.7 | 62.4 |

TABLE 2-continued

| Example | Dipyridyl Compound Formula | (g) | Reactor Pressure (N/m²) | VOSO₄ (g) | Temp. (°C.) | Time (hours) | Conversion (%) | Selectivity (%) |
|---|---|---|---|---|---|---|---|---|
| 17[a] | 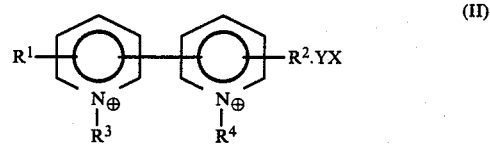 .2Br | 1.6 | $1.4 \times 10^6$ | 0.73 | 80 | 1.25 | 98 | 78 |
| 18[b] | 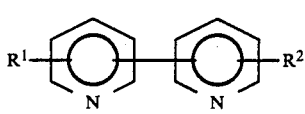 .2Cl | 4.06 | $3.1 \times 10^5$ | 1.45 | 68 | 2.6 | 95 | 88 |

[a] 20 g of N-phosphonomethyliminodiacetic acid was used
[b] 32.09 g of N-phosphonomethyliminodiacetic acid was used

EXAMPLE 19

The procedure of Example 10 is repeated except that manganese and cerium are substituted for the cobalt. Improved results are achieved over the control without the dipyridyl compound.

EXAMPLE 20

The procedure of Example 10 is repeated except that iron, nickel, chromium, ruthenium, aluminum and molybdenum are substituted for the cobalt. Improved results are achieved over the control without the dipyridyl compound.

Although the invention has been described in terms of specified embodiments, which are set forth in considerable detail, it should be understood that this by way of illustration only, and that alternative embodiments and operating techniques will become apparent to those skilled in the art in view of the disclosure. For example, there are numerous other dipyridyl compounds known to those skilled in the art that are not described in the examples. For example, there are compounds such as 1,1-di-β-hydroxyethyl-4,4'-bipyridinium dibromide, 1,1'-di-β-carboxyethyl-4,4'-bipyridinium dichloride, 1,1'-ethylene-5,5'-dimethyl-2,2'-bipyridinium dibromide, 1,1'-ethylene-4,4'-dimethyl-2,2'-bipyridinium dibromide, and 1,1'-trimethylene-2,2'-bipyridinium dibromide. Such compounds may be substituted for the dipyridyl compounds of the present invention provided that the substituents do not cause a deleterious effect on the selectivity to N-phosphonomethylglycine. Accordingly, modifications can be made without departing from the spirit of the described invention.

What is claimed is:

1. A process for the production of N-phosphonomethylglycine comprising contacting N-phosphonomethyliminodiacetic acid with a molecular oxygen-containing gas in the presence of a catalyst selected from the group consisting of the salts and salt complexes of manganese, cobalt, iron, nickel, chromium, ruthenium, aluminum, molybdenum, vanadium and cerium, and an effective amount of a dipyridyl compound represented by the formula:

$$R^1-\underset{N}{\bigcirc}-\underset{N}{\bigcirc}-R^2 \quad (I)$$

wherein $R^1$ and $R^2$ are independently selected from the group consisting of hydrogen, alkyl having from one to about 18 carbon atoms, ortho-phenylene, oxygen, sulfur, $SO_2$, $SO_3$, $N-R^5$ wherein $R^5$ is alkyl having from one to six carbon atoms and $R^1$ and $R^2$ together can form a bridge with groups selected from alkylene having from one to about six carbon atoms wherein the alkylene bridge can contain branching or double bonds; or salts thereof represented by the formula $$R^1-\underset{\underset{R^3}{N_\oplus}}{\bigcirc}-\underset{\underset{R^4}{N_\oplus}}{\bigcirc}-R^2.YX \quad (II)$$

wherein $R^1$ and $R^2$ are as defined above, Y is one or two depending on whether X is a dianion or a monoanion, and X is selected from the group consisting of halide, sulfate and nitrate, phosphate, and perchlorate; and $R^3$ and $R^4$ are individually selected from the group consisting of hydrogen or alkyl having from one to about 18 carbon atoms, and $R^3$ and $R^4$ together can form a bridge with groups selected from alkylene having from one to about six carbon atoms wherein the alkylene bridge can contain branching or double bonds.

2. A process of claim 1 wherein the dipyridyl compound concentration is at least 0.005 molar.

3. A process of claim 1 wherein the dipyridyl compound concentration is between 0.01 and 0.5 molar.

4. A process of claim 2 wherein the catalyst salt concentration is between 0.1 molar and 0.001 molar total metal ion concentration.

5. A process of claim 1 wherein the dipyridyl compound is a 4,4-dipyridyl compound.

6. A process of claim 5 wherein $R^1$ and $R^2$ are each methyl.

7. A process of claim 1 wherein the catalyst is selected from the group consisting of the salts of cobalt, manganese, vanadium and cerium.

8. A process of claim 7 wherein the catalyst is a vanadium salt.

9. A process of claim 7 wherein the catalyst is a cobalt salt.

10. A process of claim 1 wherein the dipyridyl is a salt represented by Formula II above.

11. A process of claim 10 wherein Y is two and X is halide ions.

12. A process of claim 11 wherein X is bromide ions.

13. A process of claim 10 wherein the dipyridyl compound concentration is at least 0.005 molar.

14. A process of claim 13 wherein the dipyridyl compound concentration is between 0.01 and 0.5 molar.

15. A process of claim 13 wherein the catalyst is selected from the group consisting of the salt and salt complexes of cobalt, manganese, vanadium and cerium.

16. A process of claim 15 wherein the catalyst salt concentration is between 1 molar and 0.001 molar total metal ion concentration.

17. A process of claim 1 wherein $R^3$ and $R^4$ together are selected from alkyl having from one to about six carbon atoms to form a bridge to provide a dipyridyl compound represented by the formula:

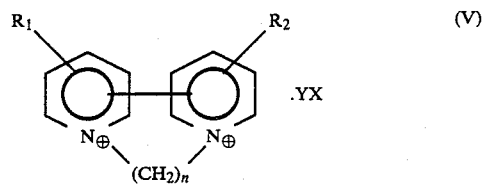

wherein X is chloride or bromide ion and n is between 1 and 18.

18. A process of claim 17 wherein n is 2.

19. A process of claim 18 wherein X is bromide ion.

20. A process of claim 17 wherein the catalyst is selected from the group consisting of the salts of cobalt, manganese, vanadium and cerium.

21. A process of claim 20 wherein the dipyridyl compound concentration is at least 0.01 molar.

22. A process of claim 21 wherein the catalyst salt concentration is between 1 molar and 0.001 molar total metal concentration.

23. A process of claim 22 wherein the catalyst is a cobalt salt.

24. A process of claim 22 wherein the catalyst is a vanadium salt.

25. A process of claim 1 whrein the N-phosphonomethyliminodiacetic acid is present as a slurry.

* * * * *